United States Patent [19]

Lau et al.

[11] Patent Number: 5,158,548
[45] Date of Patent: Oct. 27, 1992

[54] METHOD AND SYSTEM FOR STENT DELIVERY

[75] Inventors: Lilip Lau, Cupertino; William M. Hartigan, Fremont, both of Calif.

[73] Assignee: Advanced Cardiovascular Systems, Inc., Santa Clara, Calif.

[21] Appl. No.: 735,195

[22] Filed: Jul. 24, 1991

Related U.S. Application Data

[63] Continuation of Ser. No. 514,108, Apr. 25, 1990, abandoned.

[51] Int. Cl.$^5$ .......................................... A61M 29/00
[52] U.S. Cl. ...................................... 604/96; 604/164
[58] Field of Search ................................ 604/164–167, 604/96–104, 280, 282

[56] References Cited

U.S. PATENT DOCUMENTS

| | | | |
|---|---|---|---|
| 3,868,956 | 3/1975 | Alfidi et al. | 604/96 X |
| 4,323,071 | 5/1990 | Simpson et al. | 604/96 X |
| 4,332,254 | 6/1982 | Lundquist | 604/96 X |
| 4,439,185 | 3/1984 | Lundquist | 604/97 |
| 4,468,224 | 8/1984 | Enzmann et al. | |
| 4,512,338 | 4/1985 | Balko et al. | 604/96 X |
| 4,516,972 | 5/1985 | Samson | 604/282 |
| 4,538,622 | 9/1985 | Samson et al. | 604/170 X |
| 4,553,545 | 11/1985 | Maass et al. | 604/104 |
| 4,554,929 | 11/1985 | Samson et al. | 604/95 X |
| 4,569,347 | 2/1986 | Frisbie | 604/164 X |
| 4,571,240 | 2/1986 | Samson et al. | 604/96 |
| 4,572,186 | 2/1986 | Gould et al. | 604/104 X |
| 4,616,652 | 10/1986 | Simpson | 604/280 X |
| 4,655,771 | 4/1987 | Wallsten | 604/281 X |
| 4,723,549 | 2/1988 | Wholey et al. | 604/101 X |
| 4,733,665 | 3/1988 | Palmaz | 604/96 X |
| 4,739,762 | 4/1988 | Palmaz | 604/96 X |
| 4,748,982 | 6/1988 | Horzewski et al. | 604/102 X |
| 4,748,986 | 6/1988 | Morrison et al. | 604/170 X |
| 4,762,128 | 8/1988 | Rosenbluth | 604/96 X |
| 4,790,315 | 12/1988 | Mueller, Jr. et al. | |
| 4,848,342 | 7/1989 | Kaltenbach | 604/104 X |

FOREIGN PATENT DOCUMENTS 183372 10/1985 European Pat. Off. .
57-89859 6/1982 Japan .

Primary Examiner—John D. Yasko

[57] ABSTRACT

A stent delivery system having an expandable stent in a contracted condition positioned on an expandable member, such as an inflatable balloon, disposed on the distal portion of an elongated catheter body. A guidewire extends through an inner lumen within the elongated catheter body and out its distal end. A tubular protective sheath is secured by its distal end to the portion of the guidewire which extends out of the distal end of the catheter body and fits over the rolled up stent mounted on the expandable member on the distal end of the catheter body. The catheter assembly is advanced to a desired location within a patient's body lumen, such as the patient's arterial system, with the sheath in place over the stent. Once in proper position, the guidewire is advanced distally in order to remove the attached sheath and completely expose the stent. The expandable member on the catheter is expanded to expand the stent. The stent is preferably self-locking in the expanded condition so that the expanded expandable member can be contracted and the catheter can be removed therefrom.

15 Claims, 6 Drawing Sheets

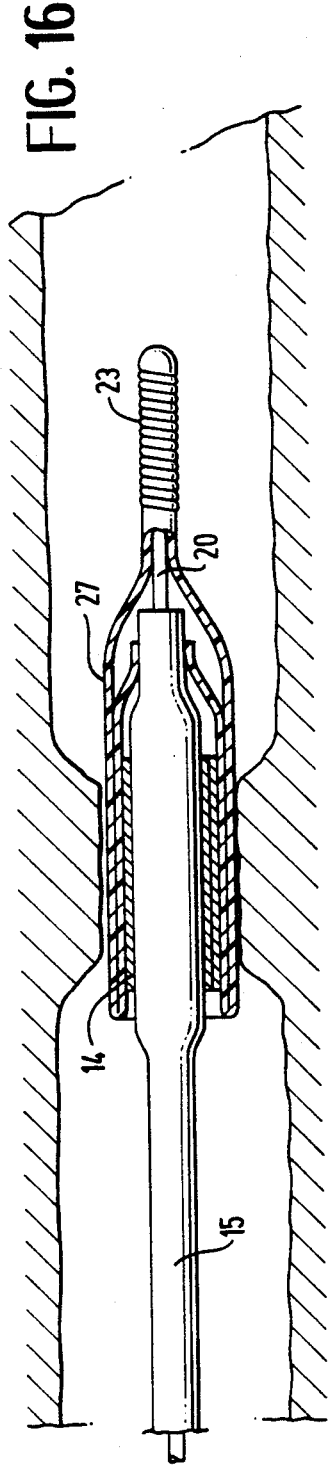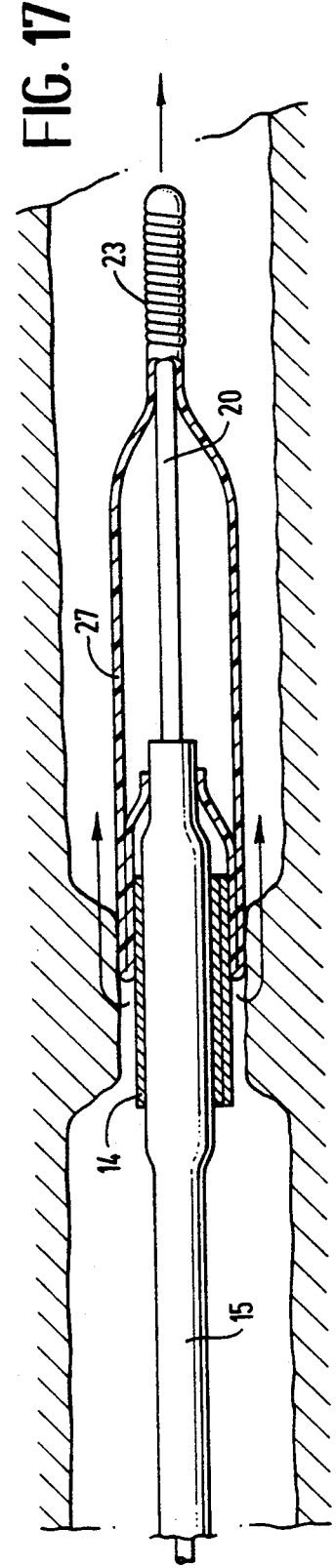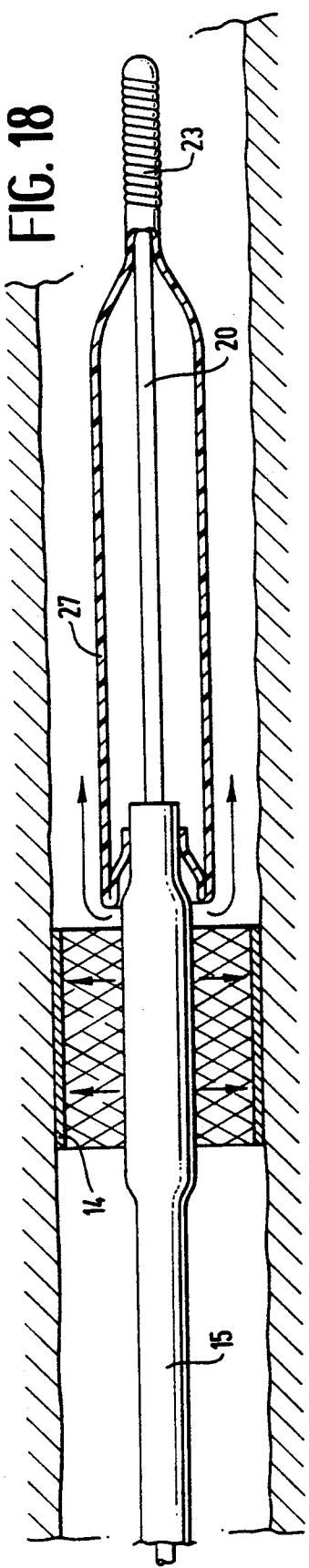

METHOD AND SYSTEM FOR STENT DELIVERY

This is a continuation of the U.S. patent application Ser. No. 07/514,108 which was filed on Apr. 25, 1990 now abandoned.

BACKGROUND OF INVENTION

This invention is related to the delivery of expandable devices commonly called "stents" within a body lumen such as an artery and the expansion of the stent therein to maintain the patency of the body lumen. The invention is particularly suitable for the delivery of stents after angioplasty procedures.

Percutaneous transluminal coronary angioplasty (PTCA) is now a widely practiced procedure for treating coronary artery disease. In a typical PTCA procedure, a dilatation catheter having an inflatable, relatively inelastic balloon on the distal end thereof is advanced through a patient's arterial system until the deflated balloon crosses an atherosclerotic lesion to be dilated. The balloon is inflated to a predetermined size with radiopaque liquid at relatively high pressures (e.g. up to 8 atmospheres or more) to compress the atherosclerotic plaque and to dilate the artery in the stenotic region. After dilation the balloon is then deflated so that the catheter can be removed. Due to the enlarged arterial passageway, increased blood flow results.

In typical PCTA procedures, a guiding catheter having a performed distal end is first percutaneously introduced into the patient's arterial system and advanced until the distal tip of the catheter is disposed in the ostium of a coronary artery. A guidewire is slidably disposed within an inner lumen of a dilatation catheter and both are advanced through the guiding catheter to the distal end thereof. The guidewire is first advanced out of the distal tip of the guiding catheter into the patient's coronary anatomy until the distal end of the guidewire crosses the lesion to be dilated. The physician usually shapes the distal end of the guidewire to facilitate steering it through the patient's tortuous coronary arteries. Once the guidewire is in place, the dilatation catheter is then advanced out of the distal tip of the guiding catheter over the guidewire until the deflated balloon on the distal end of the dilatation catheter is positioned across the lesion. The balloon is inflated to a suitable pressure to dilate the stenosis, deflated, and then removed from the patient's vasculature.

For a more detailed description of the angioplasty procedures and the devices used in such procedures, reference is made to U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); U.S. Pat. No. 4,554,929 (Samson et al); U.S. Pat. No. 4,569,347 (Frisbie); U.S. Pat. No. 4,571,240 (Samson et al); U.S. Pat. No. 4,616,652 (Simpson) and U.S. Pat. No. 4,748,982 (Horzewski et al) which are hereby incorporated in their entirety by reference thereto.

On occasions the inflation of the balloon during angioplasty causes a dissection in the arterial lining, e.g. the stenotic plaque or the arterial intima. When the balloon is deflated after such a dilation, blood can flow between the arterial wall and the dissected lining constricting the flow passage therein or causing a section of the dissected lining, commonly called a "flap," to be forced into the flow passageway thereby partially or completely blocking the blood flow through the artery.

Several methods have been proposed to resecure a dissected lining to the artery wall. For example, the dilatation catheter can be removed after the angioplasty procedure has been performed and replaced with a catheter having an expandable member at the distal end which allows for the perfusion of blood through the expandable member when expanded. In this method, the expanded member presses the dissected tissue lining against the arterial wall for an extended period until natural healing can result in the resecuring of the dissected lining to the arterial wall. Blood perfuses through the expanded member so that ischemic conditions are minimized or eliminated distal to the expanded member. However, these lining repair procedures usually require leaving the catheter with the expanded member in place for an extended period, e.g., several hours or more, in order to ensure that the lining has been properly resecured to the arterial lining. Suitable catheters for this purpose are disclosed in U.S. Pat. No. 4,790,315 and copending U.S. patent application Ser. No. 283,729 filed Dec. 13, 1988, U.S. patent application Ser. No. 404,815 filed Sep. 8, 1989, and U.S. patent application Ser. No. 404,818 filed Sep. 8, 1989, each of which are incorporated herein in their entirety by reference thereto.

Much development work has also been recently performed on the utilization of expandable stents in situations where long term expansion in an arterial or other bodily lumen is desired, such as in the instances described above. Expandable stents and their method of use are described in U.S. Pat. No. 3,868,956, (Alfidi et al); U.S. Pat. No. 4,512,338 (Balko et al); U.S. Pat. No. 4,553,545 (Maass et al); U.S. Pat. No. 4,655,771 (Wallsten); U.S. Pat. No. 4,733,665 (Palmaz); U.S. Pat. No. 4,739,762 (Palmaz); U.S. Pat. No. 4,762,128 (Rosenbluth), Japanese application 57-89859 published Jun. 4, 1982, and European Application 0183372 published Jun. 9, 1986 which are hereby incorporated herein by reference thereto. While this development work has been promising, no reliable and easily usable system has yet been developed which allows for the delivering an expandable stent to a desired location within a body lumen, particularly the coronary arteries, fixing the stent in an expanded condition within the bodily lumen and then removing the delivery system leaving the expanded stent in place. The present invention satisfies the need for such a stent delivery system.

SUMMARY OF THE INVENTION

This invention is directed to an expandable stent delivery system, which is particularly suitable for use in coronary arteries.

The stent delivery system of the present invention includes an elongated catheter body having an expandable member such as an inflatable balloon on the distal portion thereof with a constricted expandable stent mounted on the expandable member. A guidewire extends through an inner lumen of the catheter body and out an axial opening in the distal end of the catheter. A tubular protective sheath is fixed by its distal end to a portion of the guidewire which extends out of the distal end of the catheter body. In one embodiment of the invention, the tubular protective sheath is self supporting and has an inner diameter which is sufficiently large so that the sheath can easily slide over the constricted stent when mounted onto and removed from the expandable member on the distal end of the catheter body. In an alternative embodiment of the invention, the sheath is made of elastomeric or rubber-like materials so as to fit snugly over the constricted stent with one end of the sheath secured to the guidewire and one end secured to the end of the catheter or the balloon thereof.

Means are provided, preferably at the proximal end of the catheter body, to move the guidewire through an inner lumen of the catheter to enable the sheath fixed to the distal end thereof to be moved distally and to thereby uncover the constricted stent on the expandable member. With the alternative embodiment the guidewire is moved distally with respect to the catheter to peel the snugly fitting sheath off of the stent so that it can be expanded. Once the stent is completely exposed, the expandable member disposed within the constricted stent can be expanded to expand the stent and maintain the patency of the body lumen.

Preferably, the stent is of the self-locking variety so that it automatically locks in the expanded condition to enable the catheter body and the expandable member fixed thereto to be removed. A particularly suitable self-locking stent is described and claimed in copending U.S. patent application Ser. No. 283,729, filed on Dec. 13, 1988. The stent design discussed in this application has an open, reticulated structure which allows blood to flow through the cylindrically shaped walls thereof and bathe the dissected tissue after the stent is expanded into place to accelerate the healing process of the tissue.

The presently preferred expandable means on the distal end of the catheter is an inflatable balloon but other expanding devices are contemplated such as mechanical expanding devices formed of metal braids which expand when the ends thereof are axially moved closer together.

The delivery system of the invention is percutaneously introduced into the patient's arterial system in a conventional Seldinger technique commonly employed in PTCA. The guidewire is steerable so that the entire stent delivery assembly can be steered through the patient's arterial system until the stent is positioned at the desired arterial location. Once the stent is in the desired location, the guidewire is moved distally with respect to the delivery catheter a sufficient distance so that the protective sheath which has its distal end fixed to the guidewire is completely removed from the constricted stent. The balloon or other expandable member is expanded to expand the stent within the stenosis, pressing the stent against the arterial lining and preferably locking the stent in place. The diameter of the expandable member may then be reduced to disengage the catheter delivery system from the expanded stent and to facilitate its removal from the body lumen.

The delivery system of the present invention allows for the rapid and safe deployment of an expandable stent within a patient's vascular system or other bodily lumen and the quick removal of the delivery system after the stent is expanded at the desired location within the lumen.

These and other advantages of the invention will become more apparent from the following detailed description thereof and the accompanying exemplary drawings.

BRIEF DESCRIPTION OF THE DRAWINGS

FIG. 16 is an elevational view, partially in section, of an alternate embodiment of the invention;

FIG. 17 is an elevational view of the alternative embodiment show in FIG. 16 with the guidewire extended to peel off the protective sheath; and FIG. 18 is an elevational view as in FIG. 17 with the sheath further removed and the stent expanded.

DETAILED DESCRIPTION OF THE INVENTION

Figure 1:
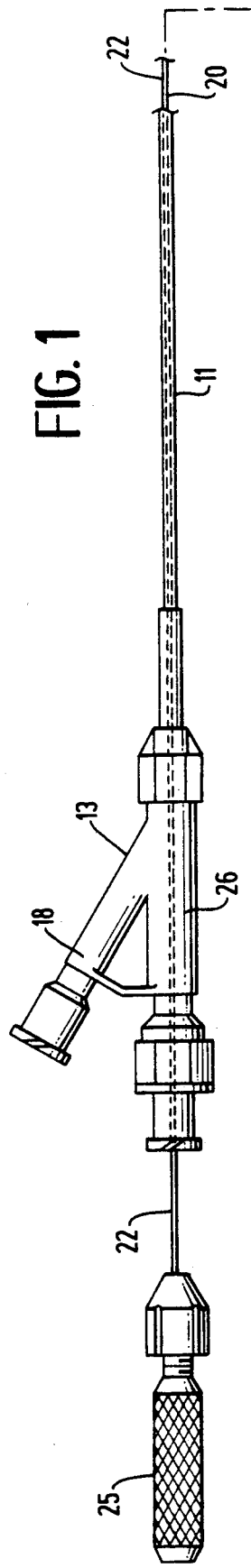
FIG. 1 is an elevation view, partially in section, of a stent delivery system embodying features of the invention.
Figure 2:
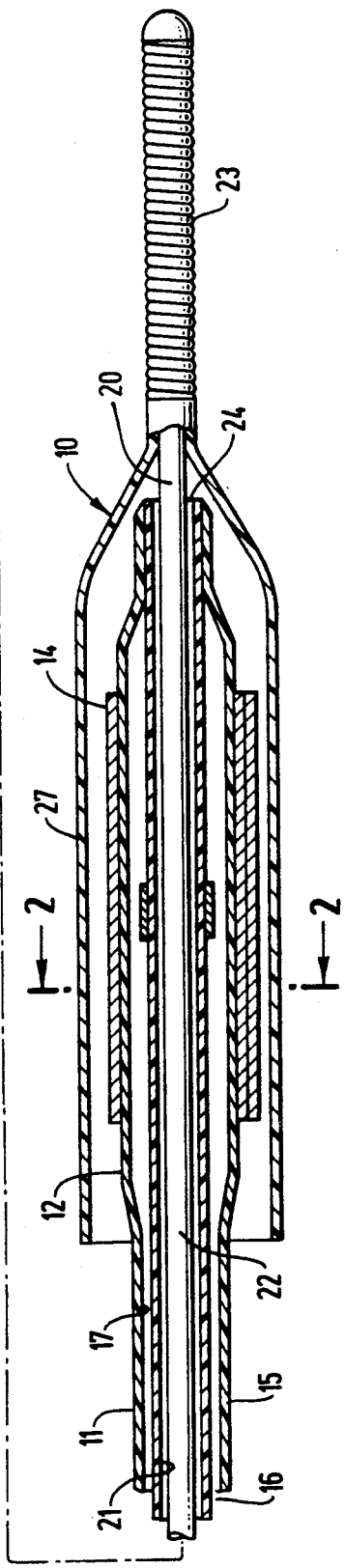
FIG. 2 is a transverse cross-sectional view taken along the lines 2—2 shown in FIG. 1.
Figure 3:
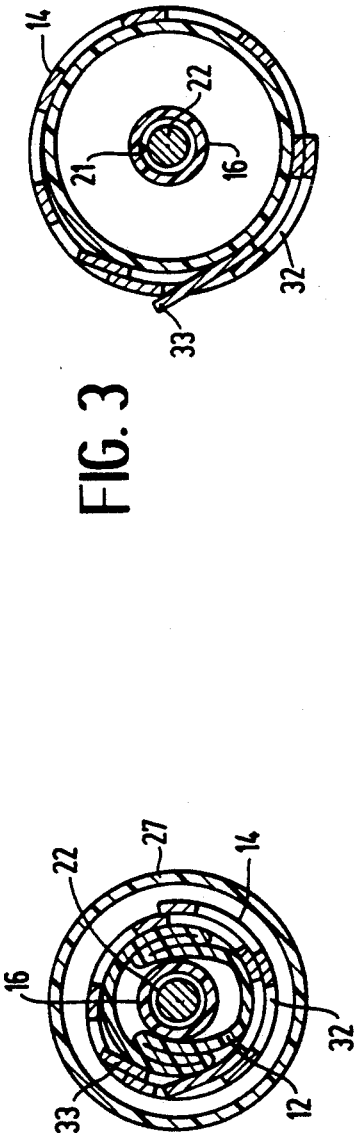
FIG. 3 is a transverse cross-sectional view of the delivery system as shown in FIG. 2 with the balloon and stent in an expanded condition.

FIGS. 1–4 illustrate a stent delivery system 10 which embodies features of the invention. The delivery system 10 generally includes an elongated catheter body 11, an inflatable balloon 12 on the distal portion of the catheter body and an adapter 13 on the proximal portion of the catheter body. The stent 14 to be delivered is mounted about the balloon 12 in a rolled up state having a relatively small diameter as best shown in FIGS. 1 and 2.

The catheter body 11 has an outer tubular member 15 and an inner tubular member 16 concentrically disposed therein which define between them an annular inflating lumen 17 for the delivery of inflation fluid to the interior of the balloon 12. Arm 18 of the adapter 13 is in fluid communication with annular lumen 17 and is adapted to be connected to a syringe-like pumping device such as is described in U.S. Pat. No. 4,439,185, previously incorporated herein, to inflate the balloon 12.

A guidewire 20 is slidably disposed within the inner lumen 21 of inner tubular member 16. It generally comprises an elongated core member 22 with a flexible coil 23 secured to the distal end of the core member. The guidewire 20 is advanced out of the distal end of the catheter body 11 through distal port 24, when the catheter is advanced into the coronary anatomy of the patient. Other types of distal guidewire constructions may be employed. For example, the distal extension of the core member 22 can terminate short of the distal tip of the coil 23 and a shaping ribbon (not shown) can extend between the core member and the distal tip of the coil. A torquing member 25 is secured to the proximal end of the core member 23 which extends out of the central arm 26 of adapter 13. The torque applied to the proximal end of the core member 23 is transmitted to the flexible distal coil 23 of the guidewire 20 so that when shaped the guidewire can be steered to a desired location within the patient's vascular system.

Figure 4:
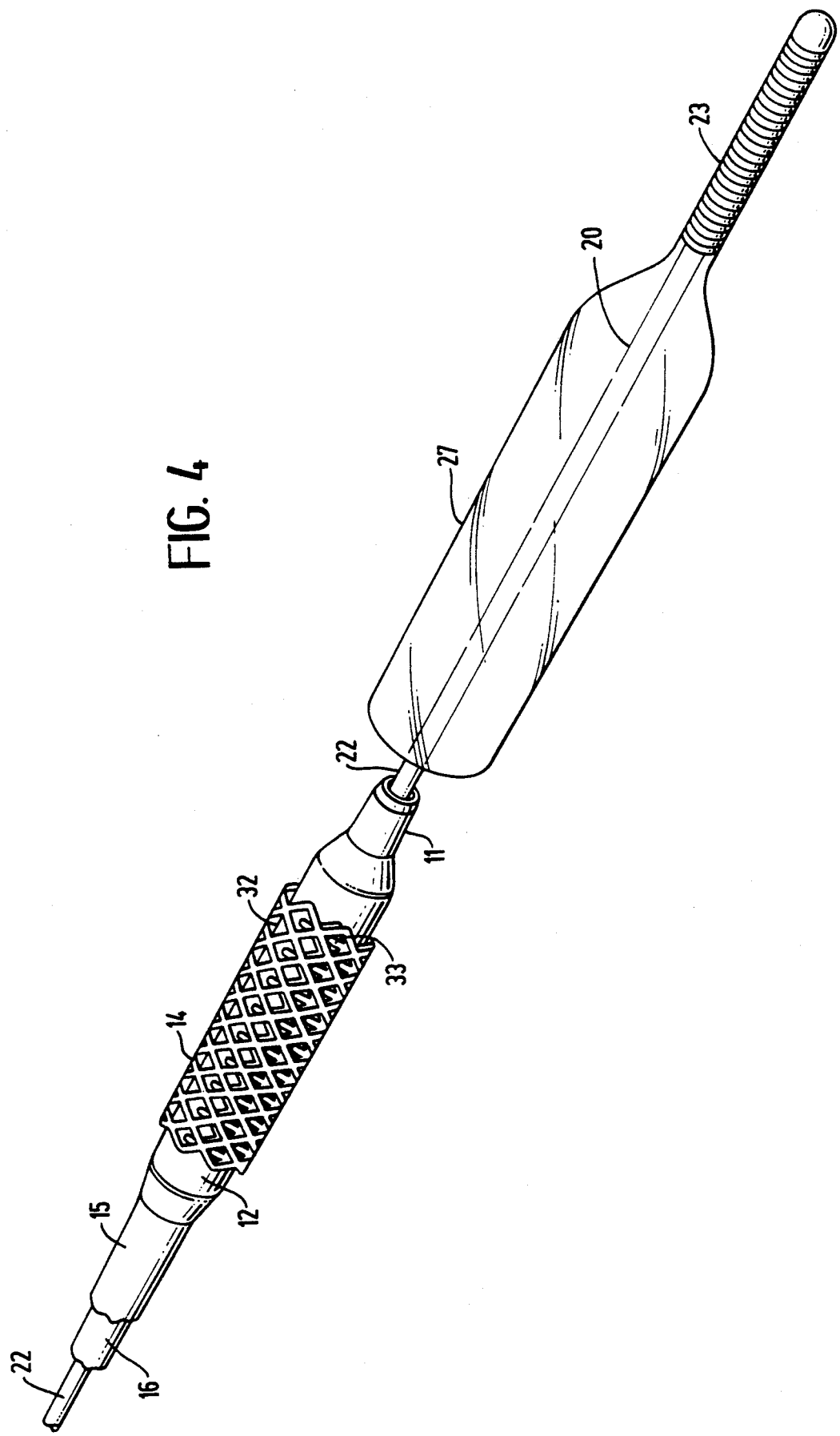
FIG. 4 is a perspective view of the stent delivery system shown in FIGS. 1 and 2 with the guidewire and attached protective sheath disposed distally to uncover the expandable stent and balloon.

A tubular protective sheath 27 is secured by its distal end by suitable means such as an adhesive to the guidewire 20. The sheath 27 has a diameter which is of sufficient size so that the sheath can easily fit over and be removed from the rolled up stent 14 mounted on the balloon 12. As shown in FIG. 4, the protective sheath 27 is removed from the balloon 12, thereby exposing the expandable stent 14, by distally advancing the guidewire 20 to which the distal end of the sheath is attached. The guidewire 20 need not be removable from the dilatation catheter 10, but it must be longitudinally movable a sufficient distance to completely remove the sheath 27 from the stent 14.

Figure 5:
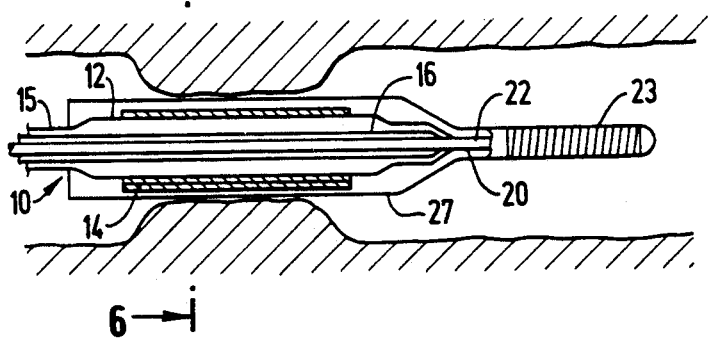
FIG. 5 is a schematic elevational view, partially in section, of the stent delivery system shown in FIG. 1 disposed within a stenotic arterial region.
Figure 6:
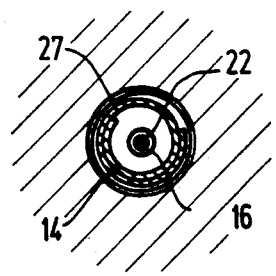
FIG. 6 is a transverse cross-sectional view taken along the lines 6—6 shown in FIG. 5.
Figure 7:
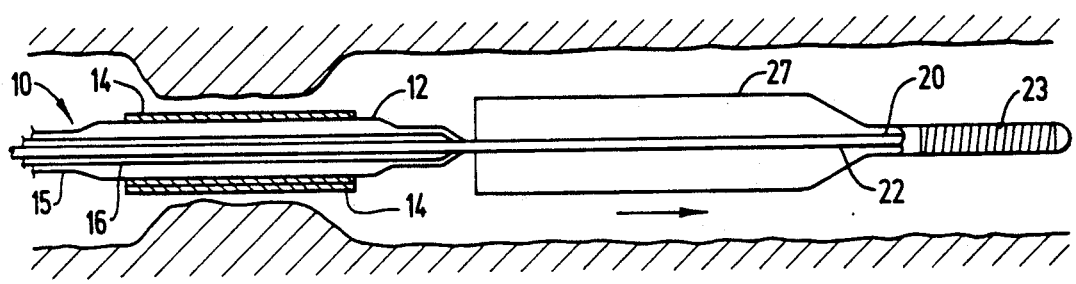
FIG. 7 is a schematic elevational view as shown in FIG. 5, partially in section, with the guidewire and sheath advanced distally from the stenotic region.
Figure 8:
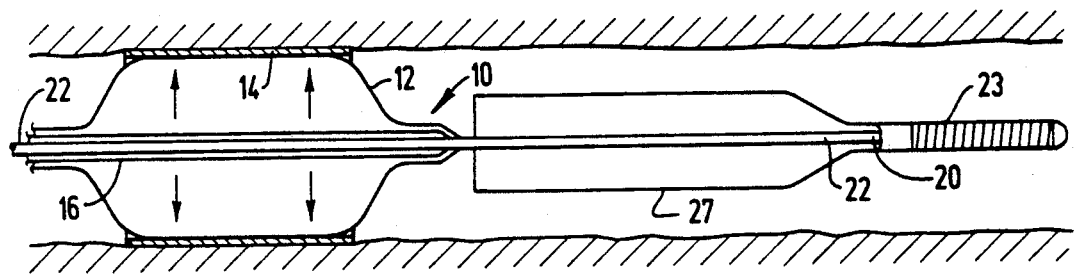
FIG. 8 is a schematic elevational view as shown in FIG. 7, partially in section, with the balloon and stent in an expanded state.
Figure 9:
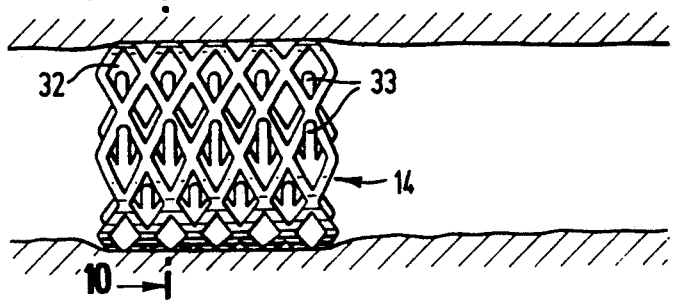
FIG. 9 is a schematic elevational view, partially in section, of a stent in an expanded condition within an artery.
Figure 10:
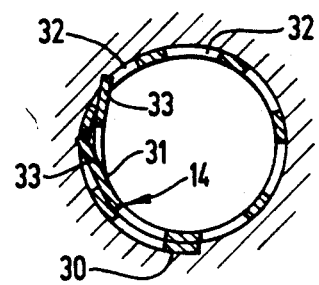
FIG. 10 is a transverse cross-sectional view taken along the lines 10—10 shown in FIG. 9.

The sequence of steps shown in FIGS. 5-9 illustrate the use of the stent delivery system of the invention to deliver a rolled-up expandable stent 14 to a stenotic region within a patient's artery. In FIGS. 5 and 6, the delivery system 10 is shown disposed within an artery with the stent 14 in a rolled-up, constricted state about the balloon 12 with the protective sheath 27 positioned over the rolled-up stent 14. In FIG. 7, the guidewire 20 has been moved distally with respect to the catheter body in order to remove the sheath 27 covering the rolled-up stent 14. In FIG. 8, the balloon 12 has been inflated to expand the stent 14 and to hold the stenotic region in a dilated condition as shown. The stent 14 is preferably of a self-locking type so that, once it is expanded and the balloon 12 deflated, it contracts slightly either from the pressure of the artery or by internal stresses within the stent itself to lock itself in the expanded condition. The deflated balloon can then be removed from within the expanded stent 14 which is pressing against the arterial lining as shown in FIGS. 9 and 10.

Figure 11:
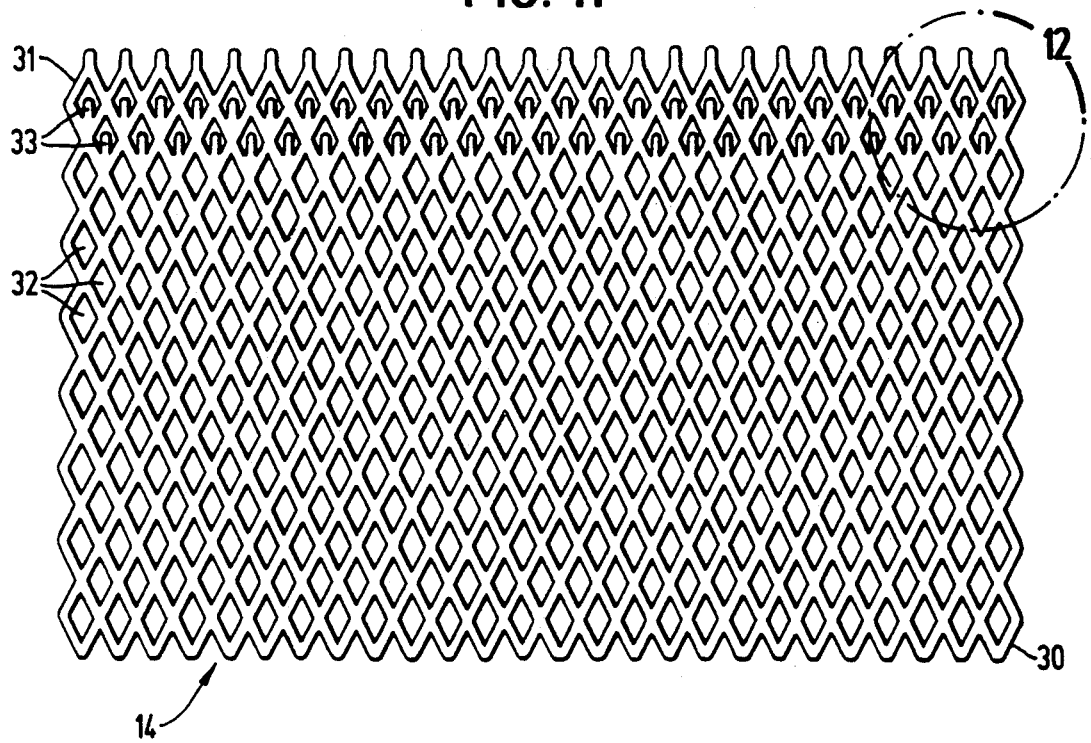
FIG. 11 is a plan view of a flat sheet from which the stent shown in the previous figures was made.
Figure 12:
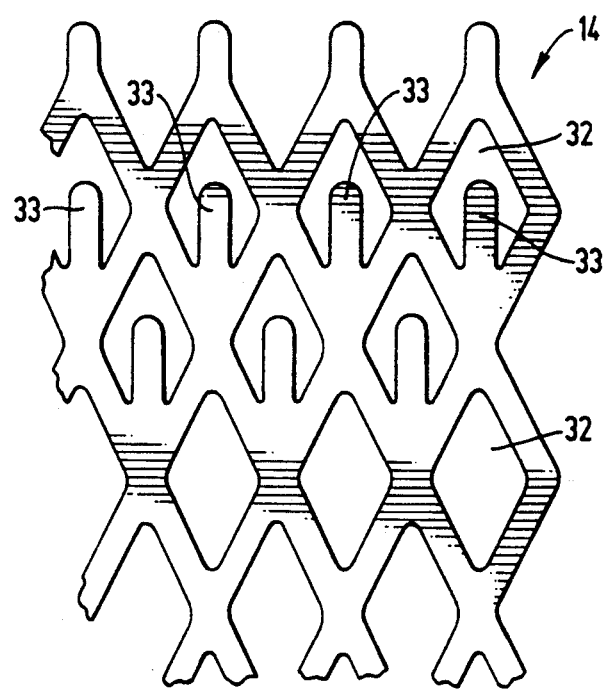
FIG. 12 is an expanded view of the area 12 shown in FIG. 4.
Figure 13:
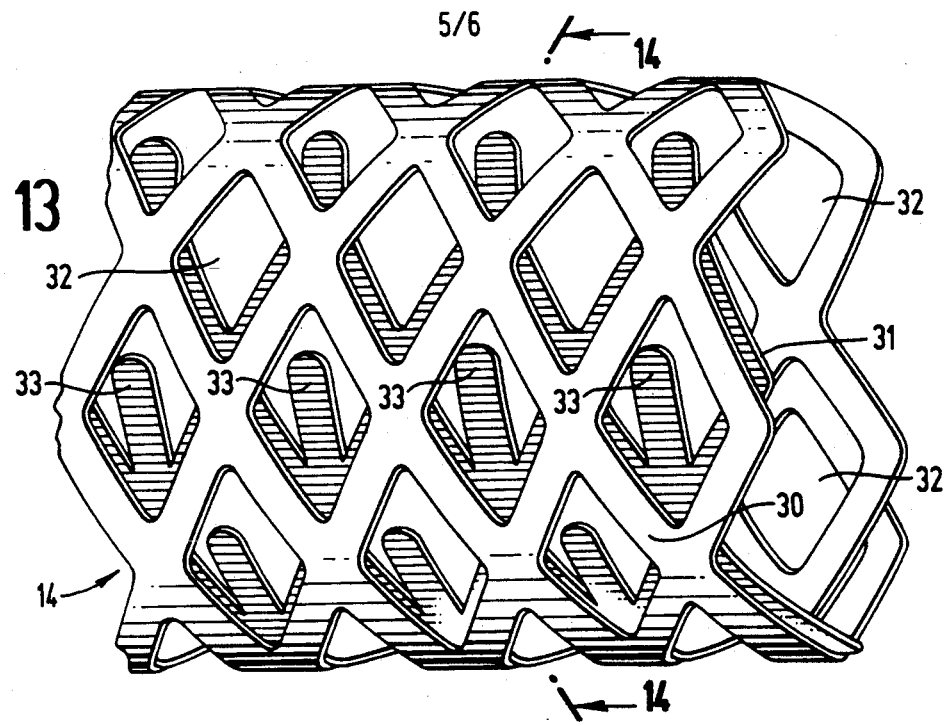
FIG. 13 is a partial perspective view of the stent shown in previous figures.
Figure 14:
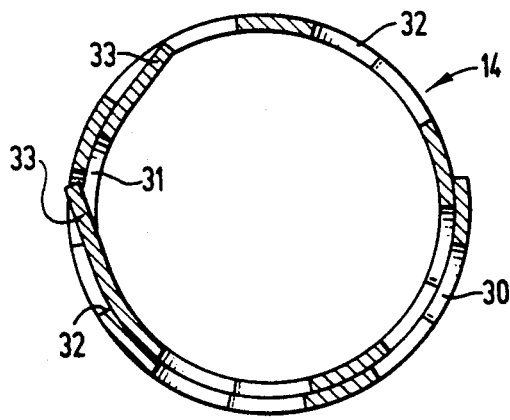
FIG. 14 is a transverse cross-sectional view taken along the lines 14—14 shown in FIG. 13.
Figure 15:
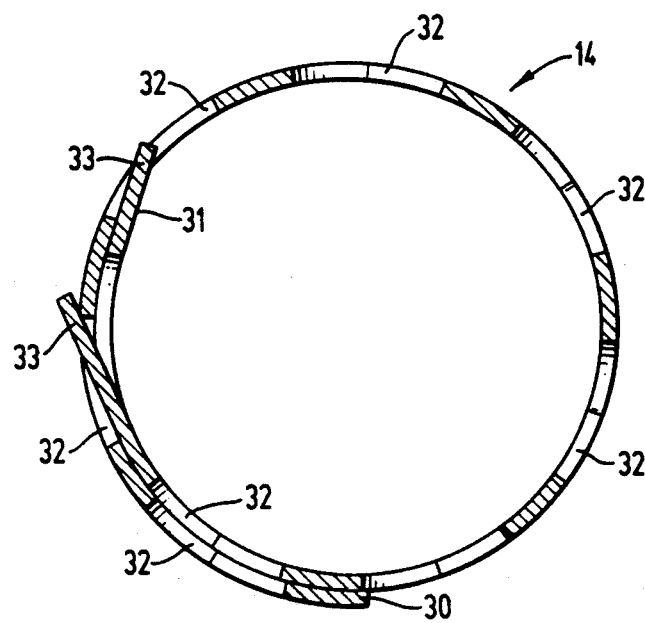
FIG. 15 is a cross-sectional view as in FIG. 14 with the stent in an expanded condition.

Structural details of the stent 14 can be found in FIGS. 11-15, particularly FIG. 12. FIG. 11 illustrates the open, reticulated structure in a flat sheet form prior to being shaped by rolling the longitudinal edge section 30 over the longitudinal edge section 31 into the cylindrically shaped stent shown in FIGS. 13 and 14. The preferred open reticulated structure includes an array of diamond shaped apertures 32. As shown in FIG. 13, fingers 33 are provided which project into the diamond-shaped apertures 32. When the stent 14 is rolled up as shown in FIGS. 13 and 14, the fingers 33 project tangentially from the rolled-up cylindrically shaped surface and point in the same direction as of the movement of the overlaying section when the stent unrolls during the expansion thereof. The pressure of the artery wall or the elasticity of the rolled up sheet will cause the expanded stent to contract somewhat thereby causing the fingers 33 to project through the diamond-shaped apertures 32 therein and to engage the perimeter of such apertures and to lock the stent in the expanded condition. See FIGS. 10 and 15. The open reticulated structure allows the stent 14 to be expanded and held in an expanded state having different diameters depending upon the degree of expansion of the stent. The number and location of the fingers 33 can be varied depending upon the needs of the intended use of the stent 14.

The materials of construction and the methods of manufacturing of the stent and delivery system can be of a conventional nature which are well known to those skilled in the art. The catheter body may be made of suitable polymers such as polyethylene, polyester, polyimide and the like. The balloon 12 and the protective sheath 27 can be bonded to their supporting members by suitable means, such as acrylonitrile based adhesives. In the embodiment shown, the sheath 27 should be formed from material of sufficient strength and/or wall thickness so that it will retain its cylindrical shape when the mounting and the removing of the sheath from the stent 14.

The core member 22 of the guidewire 20 may be stainless steel, and the coil 23 may be at least partially made of a highly radiopaque metal such as platinum, tungsten, rhenium, ruthenium or alloys of such metals to facilitate the fluoroscopic observation of the coil when the guidewire is disposed within the patient.

For long term use, the stent 14 should be made of suitable biocompatible material such as steel or tungsten. The flat sheet which forms the stent 14 may be of any suitable length and width depending upon the size of the body lumen into which it will be disposed. For coronary artery use typically the length will be about 1.5 to about 4 cm, the width about 0.5 to about 1.5 cm and the thickness about 0.02 to about 0.125 mm.

FIGS. 16-18 illustrate an alternate embodiment of the invention wherein the sheath 27 is secured by its distal end to the core member 22 and by its proximal end to the distal end of the catheter body 11. The sheath 27 is doubled over the stent 14 and preferably snugly fits thereover. The sheath 27 is formed of more flexible material than is the previously discussed embodiment and may be made from a wide variety of elastomeric material, such as polyurethane and rubber.

The sequence shown in FIGS. 16-18 illustrates the operation of the device which is essentially the same as shown in FIGS. 5-9. In FIG. 16 the device as introduced into the patient's artery and advanced therein through the stenosis. In FIG. 17 the flexible sheath 27 is removed from the stent 14. The guidewire 20 is moved distally as with the embodiment shown in FIG. 1, and this movement peels the flexible elastomeric sheath 27 from the stent 14. As shown in FIG. 18 the stent 14 is expanded by the expansion of the balloon 12 as with the previously described embodiment. Once the stent 14 is expanded and locked into place, the catheter delivery system 10 and guidewire 20 can be removed from the patient's artery.

While the invention has been described herein in terms of certain preferred embodiments, those skilled in the art will recognize that various modifications can be made. For example, the guidewire receiving lumen can be relatively short and extend about 10 to 40 cm from the distal end of the catheter and be provided with a slit proximal to the expandable member as described in U.S. Pat. No. 4,748,982 to facilitate the rapid exchange thereof. Other modifications and improvements can be made without departing from the scope of the invention.

What is claimed is:

1. A stent delivery system, comprising:
   a) an elongated catheter body having an expandable member on the distal end thereof and at least one inner lumen extending therein;
   b) an expandable stent which is disposed about the expandable member in a contracted condition;
   c) a guidewire which is disposed within the inner lumen of the catheter body and which has a distal portion extending out the distal end of the catheter body;
   d) a protective tubular sheath which is secured by its distal end to the distal portion of the guidewire extending out of the distal end of the catheter body and which fits over the stent disposed about the expandable member;
   e) means to move the guidewire distally through the inner lumen to remove the sheath from the stent;
   f) means to expand the expandable member to thereby expand the stent surrounding the expandable member;
   g) means to hold the stent in an expanded condition; and
   h) means to contract the expanded member so that it can be removed from the stent in the expanded condition.

2. The stent delivery system of claim 1 wherein the expandable member is an inflatable balloon.

3. The stent delivery system of claim 2 wherein the elongated catheter body has a second lumen extending therein which is in fluid communication with the interior of the inflatable balloon to direct inflation fluid therein.

4. The stent delivery system of claim 1 wherein the distal end of the tubular protective sheath is tapered.

5. The stent delivery system of claim 1 wherein the stent is formed of flat sheet which is rolled up into the contracted condition and mounted onto the expandable member.

6. The stent delivery system of claim 5 wherein the stent has overlapping longitudinal edge sections, the inner most edge section having fingers which project outwardly and engage apertures in the outer overlaying longitudinal sections to lock the stent in an expanded condition when the stent is expanded.

7. The stent delivery system of claim 1 wherein the stent has an open reticulated structure.

8. The stent delivery system of claim 7 wherein the open reticulated structure comprises an array of diamond shaped apertures.

9. The stent delivery system of claim 8 wherein the diamond shaped apertures have long and short dimensions and the fingers point in the longitudinal direction.

10. The stent delivery system of claim 1 wherein the sheath has an inner diameter of sufficient size to be slid over the stent when it is disposed about the expandable member.

11. The stent delivery system of claim 1 wherein the sheath is formed of flexible material, has a proximal end secured to the distal end of the catheter body and is doubled over the stent.

12. The stent delivery system of claim 11 wherein the sheath snugly fits over the stent.

13. A method of delivering an expandable stent to a region within a patient's bodily lumen, comprising:
   a) providing a stent delivery system which includes an elongate catheter body with an expandable member on the distal end thereof and a guidewire disposed within an inner lumen in the catheter body with a distal portion of the guidewire extending out of the distal end of the catheter body with a tubular protective sheath secured by the distal end thereof to the distal portion of the guidewire;
   b) mounting an expandable stent in a contracted condition onto the expanded member
   c) disposing the protective tubular sheath over the expandable stent mounted on the expandable member
   d) advancing the stent delivery system through a patient's bodily lumen until the stent is disposed within a desired region therein;
   e) advancing the guidewire distally within the lumen to remove the protective sheath from over the mounted stent;
   f) expanding the expandable member to expand the stent thereon;
   g) locking the stent in an expanded condition; and
   h) contracting the expandable member sufficiently to facilitate removing the expandable member from within the expanded stent.

14. The method of claim 13 wherein the stent delivery system is removed from the patient's body lumen.

15. The method of claim 13 wherein the expandable member is an inflatable balloon and wherein the balloon is inflated with inflation liquid.

* * * * *